United States Patent [19]

Stock

[11] 4,097,235
[45] Jun. 27, 1978

[54] AUTOCLAVE AND AUTOCLAVE SYSTEM

[75] Inventor: Hermann Stock, Neümunster, Germany

[73] Assignee: Firma Hermann Stock, Neumunster, Germany

[21] Appl. No.: 689,914

[22] Filed: May 25, 1976

[30] Foreign Application Priority Data

Jun. 5, 1975  Germany .................... 2524909

[51] Int. Cl.² .......... A23L 1/00; A23L 3/14; A61L 3/00; A61L 3/02
[52] U.S. Cl. .................... 21/93; 21/78; 21/104; 23/290; 99/371; 99/483
[58] Field of Search ............ 21/2, 78, 93, 99, 103, 21/104, 79, 80, 86, 91, 92, 94, 97, 98; 99/359, 371, 483; 23/290

[56] References Cited

U.S. PATENT DOCUMENTS

| 999,294 | 8/1911 | Bengs | 99/371 |
|---|---|---|---|
| 1,003,952 | 9/1911 | Schmitt | 99/371 |
| 1,010,805 | 12/1911 | Rogers | 99/371 |
| 1,960,890 | 5/1934 | Bidwell | 21/98 |
| 2,102,868 | 12/1937 | Waugh | 21/93 |
| 2,119,346 | 5/1938 | Page et al. | 99/371 |
| 3,897,818 | 8/1975 | Champel | 21/98 |

*Primary Examiner*—Morris O. Wolk
*Assistant Examiner*—Bradley Garris
*Attorney, Agent, or Firm*—Toren, McGeady and Stanger

[57] ABSTRACT

A vessel comprises a cylindrical shell, which has a horizontal axis. A row of outlet openings communicate with the interior of the vessel and are spaced apart along the lowermost generatrix of the shell. An outlet manifold extends outside the vessel and communicates with said outlet openings. A row of inlet openings communicate with the interior of the vessel and are spaced apart along a second generatrix of the shell. The second generatrix is angularly spaced from the lowermost generatrix by a central angle up to 50°. An inlet manifold extends outside the vessel. A plurality of pipelines are provided, each of which connects the inlet manifold to one of the inlet openings. The vessel is included in an autoclave system, which comprises a recirculating system, which connects the outlet manifold to the inlet manifold and incorporates a heater for heating liquid and a circulating pump for recycling liquid from the outlet manifold through the heater to the inlet manifold.

17 Claims, 12 Drawing Figures

AUTOCLAVE AND AUTOCLAVE SYSTEM

SUMMARY OF THE INVENTION

This invention relates to an autoclave system which comprises a preferably cylindrical vessel, in which articles to be sterilized, e.g., cans, are to be heated for sterilization, which is effected in that a heated liquid is fed into the vessel and is withdrawn through outlet openings disposed along the lower generatrix of the vessel and is recirculated by a circulating pump to flow through a heater and back into the vessel. The invention relates particularly to a vessel which is intended to be used in such autoclave system and provided with inlet means for feeding a heated liquid and outlet means for withdrawing said liquid. Special features relate to the arrangement of said inlet and outlet means at the shell of the vessel.

Such autoclave systems are known and use water as liquid. The water may be heated in a heat exchanger or directly in that steam is injected into the water in a heating vessel. In such systems it is known to feed the liquid into the vessel at the top and to withdraw the liquid at the bottom of the vessel, and it is also known to provide top and bottom manifolds and which communicate through a row of openings with the interior of the vessel and serve to feed and withdraw the liquid. The vessel is preferably cylindrical although vessels having a shell of different shape may be used in non-agitating autoclaves, in which the articles to be sterilized are sterilized while they are at rest. When reference is made hereinafter to angles, these are center angles, which are related to the center line of the elongated vessel and are usually measured from the lowermost generatrix.

The invention relates also to rotary autoclave systems which contain in the vessel a rotary cage, which receives the articles to be sterilized and is rotated on its longitudinal axis. In such systems, the outer vessel is cylindrical. The rotation of the rotary cage results in a movement of the articles to be sterilized and causes them to be turned upside down and also results in an agitation of the liquid.

When it has been stated that the liquid is fed at the top of the known vessels, this means that the liquid is fed at the apex of the vessel or in its upper half.

The known inlet means have been found to have considerable disadvantages.

Even when heated liquids other than water are used, the specific gravity of the liquid varies with its temperature. When heated liquid is fed from above or through the upper portion of the vessel, the buoyancy of the liquid portions that have been heated to different temperatures will result in such a temperature distribution that the temperature is higher at the top than at the bottom. This is particularly true in non-agitating autoclaves. Such temperature gradient will be obtained even if the liquid is fed and withdrawn at different ends of the vessel. As a result, the articles to be sterilized which have been placed into the vessel are subjected to different temperatures during their sterilization time. The articles in the lower portion of the vessel are subjected to lower temperatures than those in the upper portion of the vessel. Because the sterilizing effect is related to the product of the time and temperature of the sterilizing treatment, either a uniform sterilization will not be ensured or the temperature gradient in the vessel requires the selection of such a time of treatment that the articles disposed in the zones which are at a lower temperature are also subjected to the elevated temperature for a time which is sufficient to effect sterilization. As a result, articles contained in zones at higher temperature are subjected to that temperature for a relatively long time. This may be undesirable, particularly with foodstuffs, which may deteriorate in color and cohesion and in essential constituents as a result of an excessively long overheating.

These disadvantages will be eliminated to a considerable extent by the provision of a rotating cage. This is not only due to the stirring function of the cage, which continuously agitates the sterilizing liquid, but also to the fact that the articles to be sterilized are moved, to a certain extent, through different zones of the vessel. This movement is restricted as regards the articles which are arranged substantially along the center of the vessel, adjacent to the axis of rotation of the rotating cage. Owing to the above-mentioned specific gravities of liquid portions which are at different temperatures, the rotation causes the cold water to flow outwardly to the shell of the vessel under a virtually centrifugal action so that the operation of an agitating autoclave system results also in a formation of zones which are at different temperatures although such zones are not so sharply defined as in a non-agitating autoclave system. Nevertheless the presence of such zones at different temperatures results in different conditions for the treatment of articles which are contained in the autoclave vessel and specifically in the rotating cage.

It is an object of the invention to provide non-agitating and particularly agitating autoclave systems which are improved in such a manner that the temperature in the vessel is more uniform throughout the height of the vessel so that the sterilization time may be minimized. As a result, energy is saved and a good sterilizing effect is ensured in conjunction with an optimum treatment of the articles to be sterilized.

This object is accomplished in that inlet openings for the heated liquid are provided, which are disposed along a generatrix that is laterally and upwardly angularly spaced from the lowermost generatrix by an angle of up to 50°. It has surprisingly been found that the feeding at such relatively low level, near the outlet openings disposed at the bottom, results in a more uniform temperature distribution throughout the cross-section of the vessel as a result of an action of the specific gravities of liquid portions that are at different temperatures.

In a particularly preferred embodiment, the liquid is fed in a direction which is tangential to the shell of the vessel because the inlet openings extend through the shell of the vessel tangentially rather than radially so that the liquid enters the vessel with a defined tangential component of velocity. In a particularly preferred embodiment, the axes of the inlet openings are directed inwardly and downwardly with respect to the shell and toward the outlet openings. Surprisingly it has been found that even an arrangement of inlet and outlet openings which are only closely spaced apart does not result in a flow of liquid along a short path from the inlet openings to the outlet openings but the inflow of the liquid produces kinetic eddies, which spread through the interior of the vessel and result in a more uniform temperature distribution. These eddies are directed upwardly and toward the center so that heat is transferred to the articles to be sterilized and the heat transfer is improved by the turbulence which is due to the tangential inflow. This will be particularly the case if the liquid consists of water that has been heated by injected steam, which has special advantages.

For certain uses, the angular spacing between the lowermost generatrix, along which the outlet openings are disposed, and the generatrix along which the inlet openings are disposed, is at least about 20°.

For many uses, it is sufficient to provide only a single row of inlet openings on one side of the vessel. In a particularly effective embodiment, rows of inlet openings are provided on both sides of the row of outlet openings. In this case the liquid flows in inwardly and downwardly on both sides and the combination of the actions of the jets gives particularly good results.

In an autoclave system comprising a rotating cage, a desirable feature resides in that the liquid enters the vessel in a tangential direction which depends on the direction of rotation and speed of rotation of the cage. In that case, a rotatry cage is used which is substantially circular in cross-section and consists of elongated track rails, bearing rings or other means connecting said side rails and carriages, which are substantially rectangular in cross-section and supported by said side rails and contain the articles to be sterilized. The movement of these profiled structures past the row of inlet openings result in a chopping action on inflowing jets of heated liquid so that in this case too the liquid enters the vessel tangentially and substantially parallel to the direction in which the periphery of the rotating cage moves past the row of inlet openings. A surprising result resides in that heated liquid which has entered the vessel is entrained by the rotating cage, particularly at its periphery, so that the above-mentioned centrifugal action of the cold liquid is opposed.

According to a preferred feature, inlet means are provided before and/or behind the row of lower outlet openings, with respect to the direction of rotation of the rotating cage, and serve to inject heated liquid in a tangential direction which is opposite to the direction of rotation of the rotating cage. This feature results not only in a particularly effective distribution but permits also of an arrangement of inlet openings at a very small distance from the row of outlet openings and before the latter with respect to the direction of rotation of the cage.

A special feature resides in that the heated liquid does not enter the vessel in a trickling flow but with such a kinetic energy that jet actions are effected in the liquid volume in the interior of the vessel. This effect can be improved further in that pipelines for feeding the liquid are coaxially connected to the outside of the inlet openings so that axial direction of the inlet openings is imparted to the liquid.

In conjunction with a vessel which is provided at its apex with a manifold for receiving liquid from a heat exchanger, a preferred feature resides in that the pipelines are connected between said manifold and the inlet openings. The manifold is suitably provided at the apex of the vessel with a row of inlet openings which are directed into the vessel from above so that liquid enters the vessel at two generatrices.

The inlet openings are suitably regularly spaced along a generatrix and are spaced up to about 50 centimeters apart. The spacing of the inlet openings may be varied in dependence on internal structural dimensions relating to carriages which are movable into the non-agitating autoclave vessel or the rotary cage so that the uniform distribution is not adversely effected even if the carriages are closely spaced apart. According to a preferred feature, the inlet openings are spaced about 20 centimeters apart.

Reference having been made hereinbefore to a feeding of liquid having a kinetic energy, a particularly preferred feature resides in that the inlet openings are formed by nozzles, which define flow passages that are constricted relative to the inlet pipes. These nozzles ensure that the inflowing heated liquid first imparts to the liquid in the vessel a movement in the feeding direction. This movement promotes the mixing of the liquid and improves the uniformity of the distribution of temperature.

According to a particularly preferred feature, valve means are provided at the inlet openings or in the pipeline connected to the inlet openings. These valve means may comprise a valve member which is rotatable on an axis that is parallel to the longitudinal axis of the vessel and has a flow passage that constitutes an inlet opening, and these valve means are adjustable to change the direction in which the liquid enters the vessel. In agitating autoclave systems, such change may be effected in dependence on the speed of rotation and/or the temperature required for the sterilization. In non-agitating autoclave systems, such adjustment is also desirable in dependence on the nature of the articles to be sterilized, particularly on the type of package, e.g., the size of cans. According to a desirable feature, the valves associated with all inlet openings of a row are adjustable in unison by a common handle. Alternatively, each valve may be individually adjusted, and particularly the setting of the valves near the ends of the vessel may differ from the setting of the valves near the middle of the length of the vessel so that the different conditions existing adjacent to the ends of the vessel can be allowed for and a uniform temperature distribution throughout the length of the vessel can be achieved.

According to a further feature, the above-mentioned inlet openings at the apex of the vessel may be adjusted to vary their exposed areas along the length of the vessel.

Embodiments of the invention will now be explained by way of example with reference to the diagrammatic drawings, in which

BRIEF DESCRIPTION OF THE INVENTION

DETAILED DESCRIPTION OF THE INVENTION

In all Figures, like reference characters designate like parts.

Whereas a cylindrical vessel 1 is shown in all embodiments, a vessel having a different cross-sectional shape could be used, particularly in a non-agitating autoclave system. A manifold 2 extends on the outside of the vessel 1 along the lowermost generatrix thereof and communicates through a series of outlet openings 3, 4, 5, etc. with the interior of the vessel. The manifold 2 is connected to a pipeline 6, which incorporates a circulating pump 7 and leads to a heater 8 for the sterilizing liquid. This heater may be a heat exchanger or a steam-jet heater, in which water is heated by injected steam. The heater is basically a flow heater, from the outlet of which at least one pipeline 9 leads to a manifold 10 or 11, which distributes the heated liquid throughout the length of the vessel. Instead of a single pipeline 9, a plurality of parallel pipelines may be used.

Figure 1:
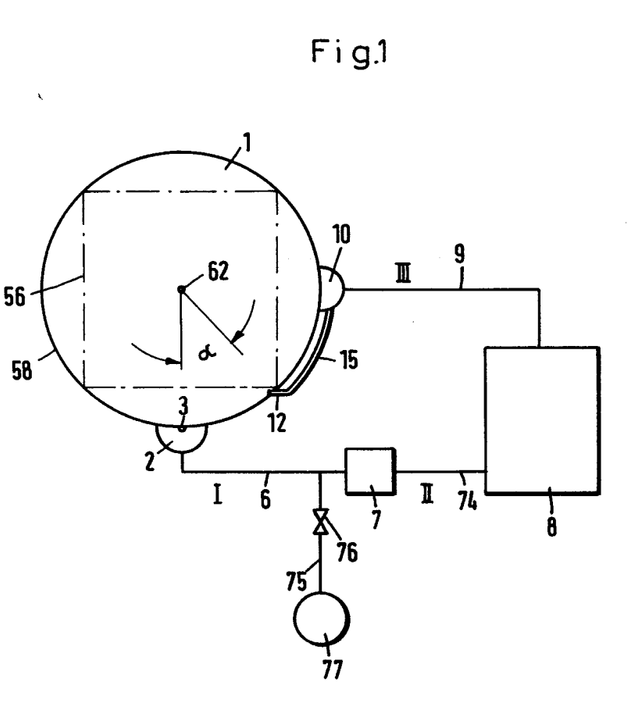
FIG. 1 is a diagrammatic end elevation showing a non-agitating autoclave system.

FIG. 1 shows a non-agitating autoclave system, which accommodates articles to be sterilized within a spaced defined by an imaginary line 56. Heated liquid is withdrawn through a row of openings, one of which is designated 3, and is received through inlet openings, which are disposed on a generatrix at 12 of the vessel in the lower portion thereof and are spaced about 20 centimeters apart. The generatrix at 12 is fairly close to the row of outlet openings 3 to 5 and is angularly spaced therefrom by a central angle α, which should be less than 50°.

The manifold 10 is spaced from the row of inlet openings 12, 13, 14 etc. and is connected to the inlet openings by curved pipelines 15, 16, 17 etc. which cause the liquid to enter the inlet openings 12 to 14 in a tangential direction. As is particularly apparent from FIG. 1, the axes of the inlet openings extend tangentially toward the row of outlet openings 3, 4, 5 and for this purpose extend substantially horizontally at the indicated generatrix at the lower portion of the vessel so that the heated liquid which enters the vessel is distributed throughout the cross-section of the vessel and delivers heat as it rises in the vessel.

Figure 9:
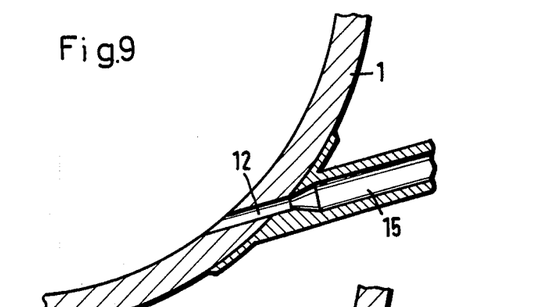
FIG. 9 is a fragmentary elevation showing a portion of a vessel and an inlet opening thereof.

Such inlet opening 12 and the pipeline 15 connected thereto are shown on an enlarged scale in FIG. 9. It is apparent that the inlet opening 12 is smaller in cross-section of flow than the pipeline 15 to form a nozzlelike constriction. The heated liquid issues from the inlet opening 12 in the form of a jet, which has kinetic energy that ensures a strong agitation.

Figure 4:
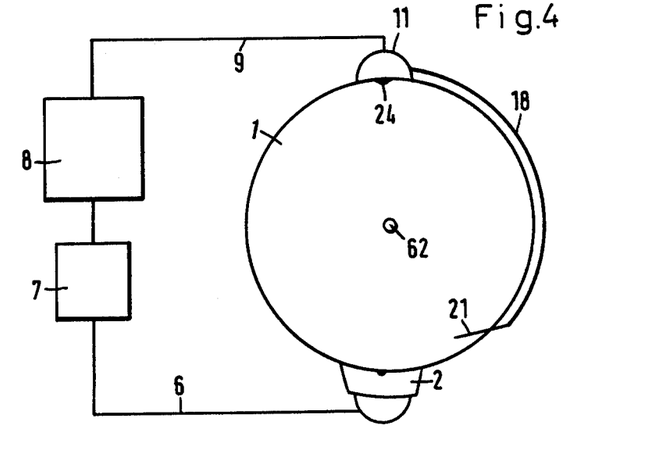
FIG. 4 is also a view which is similar to FIG. 1 and shows a further embodiment of an autoclave system.
Figures 5, 6:
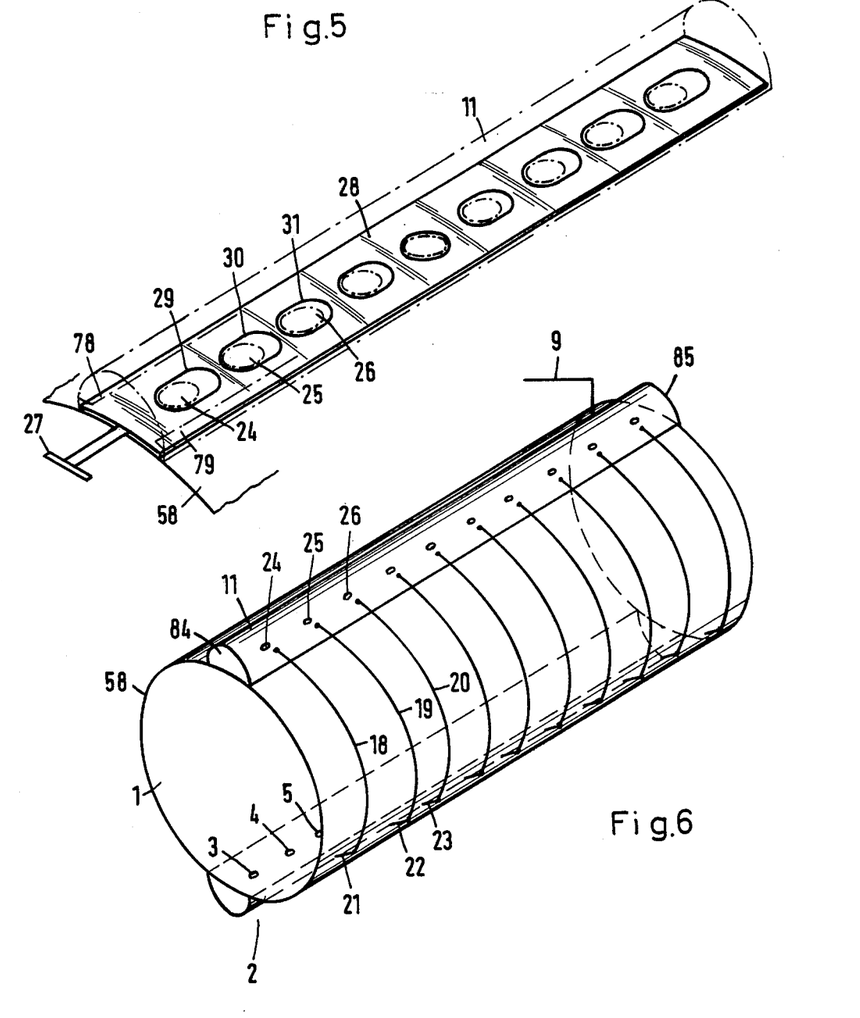
FIG. 5 is a perspective view showing details of FIG. 4.
FIG. 6 is a perspective view showing the autoclave system of FIG. 4.

In FIG. 4, the disposed near the inlet openings 12 to 14 is replaced by a manifold 11 arranged at the apex of the vessel so that the pipelines 18, 19, 20 etc. shown also in FIG. 6 and leading to the lower inlet openings 21, 22, 23 extend around more than one-fourth of the circumference of the vessel. This embodiment shown in FIG. 4 affords the advantage that a row of inlet openings 24, 25, 26 are provided also at the apex so that heated liquid enters the vessel 1 at its top and in its lower portion.

It is apparent from FIG. 5 that the upper inlet openings 24, 25, 26, etc. are adjustable. For this purpose, a gate member 28 is provided, which is movable from the outside, e.g., by means of an outwardly extending handle 27, and is formed with apertures 29, 30, 31, which are associated with respective inlet openings 24 to 26 and have different cross-sectional shapes whereas all inlet openings 24 to 26 have the same cross-sectional shape. Those of the apertures 29 to 31 which are nearer to the ends of the vessel have an increasingly elliptical shape, with major axes extending in the longitudinal direction of the gate member. The gate is movable from a basic position, in which all inlet openings 24 to 26 are uniformly exposed, to positions in which the inlet openings nearer to the middle of the length of the vessel are closed to a larger extent than the inlet openings which are nearer to the ends of the vessel and which are left exposed in a larger area.

Figure 3:
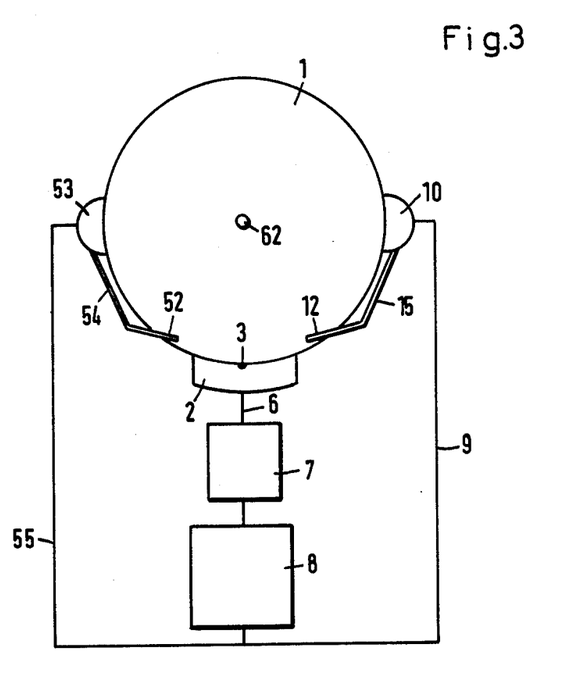
FIG. 3 is a view which is similar to FIG. 1 and shows a different embodiment of the autoclave system.

FIG. 3 shows a modification of the embodiment of FIG. 1. Inlet openings 12 etc. and 52 etc. are disposed on opposite sides of the row of outlet openings 3 to 5. The axes of all inlet openings extend tangentially inwardly and downwardly toward the generatrix along which the outlet openings are disposed. An additional manifold 53, which is disposed opposite to the manifold 10 is connected to the inlet openings 52 etc. by respective pipelines 54, which correspond to pipelines 15 to 17. In addition to the pipeline 9 leading to the manifold 10, a corresponding pipeline 55 is provided, which leads from the heater 8 to the manifold 53.

Figure 7:
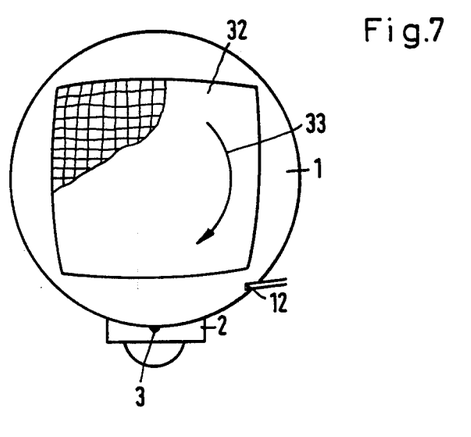
FIG. 7 is a diagrammatic end view showing an agitating autoclave system.
Figure 8:
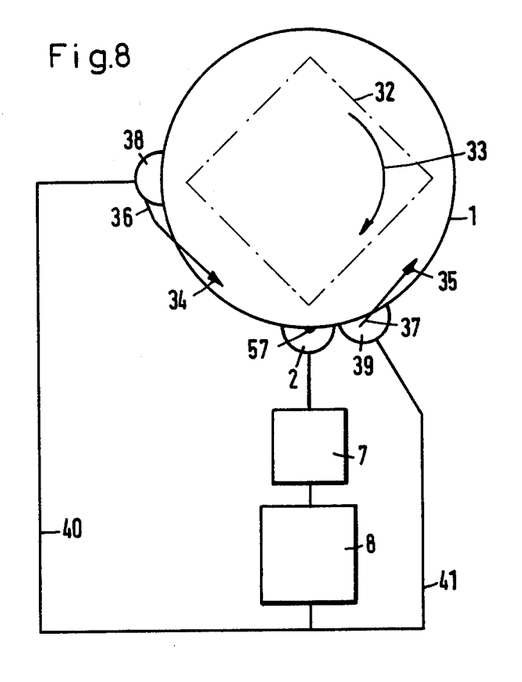
FIG. 8 is a diagrammatic end view showing another embodiment of an agitating autoclave system.

FIGS. 7 and 8 show a rotary cage 32, which is disposed in the vessel 1 and driven to rotate, e.g., in the direction of arrow 33 but may alternatively be driven to oscillate about its axis.

In FIG. 7, a row of inlet openings 12 etc. are provided as in FIG. 1 and have axes which are tangential with respect to the direction of rotation of the cage 32 and extend toward the row of outlet openings 3, 4, 5 at the lower manifold. In this way, an improved temperature distribution can surprisingly be effected although during a rotation of the cage in the direction shown the heated water which has entered the vessel does not immediately flow to the outlet openings. To this end, the kinetic energy of the heated liquid jets is utilized as well as the tendency of said heated liquid to rise because it is lighter owing to its higher temperature.

According to FIG. 8, inlet openings are provided in two rows 34, 35 and are connected by pipe sections 36, 37 to manifolds 38, 39, which are fed through pipelines 40, 41. It is apparent that the row of inlet openings 35 and 34 are respectively arranged before and behind the row of outlet openings 57 with respect to the direction of rotation 33 of the rotating cage 32 and the axes of the inlet openings of both rows 35 and 34 are tangential and opposite to the direction of rotation of the rotating cage. This modification is included.

Figure 10:
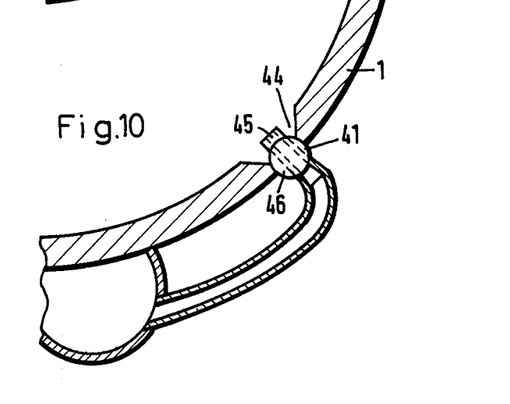
FIG. 10 is a fragmentary elevation showing a portion of a vessel according to another embodiment, which is provided with an adjustable inlet.
Figure 11:
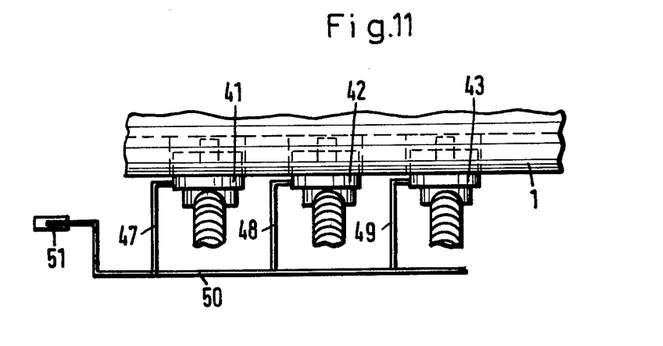
FIG. 11 shows the arrangement of FIG. 10 with a linkage which connects different inlet openings.

To enable an adjustment in view of the nature of the package of articles to be treated in a non-agitating or agitating autoclave system, and in the latter also in view of the speed and direction of rotation, a preferred feature which is illustrated in FIGS. 10 and 11 resides in that valve means 41, 43, etc. are provided at each of the openings 44 in the shell of the vessel 1 and enable an adjustment of the axes of the inlet openings. For instance, the inlet openings 45 extend through cylindrical valve members 46 having an axis of rotation which is parallel to the longitudinal axis of the vessel 1 so that the axis of each inlet opening 44 can be adjusted to any desired angular position in the shell of the vessel 1. In accordance with FIG. 11, the valve members are connected by outwardly extending rods 47, 48, 49 etc. to a common linkage 50, which is operable by a handle 51 for adjusting the valve members in unison.

As has been explained hereinbefore, the possibility of an individual adjustment of each valve enables an allowance for special conditions near the ends of the vessel. This adjustment of the directions of the axes of the inlet openings permits of a variation of said directions also in view of different packages or products to be sterilized if such different packages or products are provided in different portions of the length of the vessel.

Figure 12:
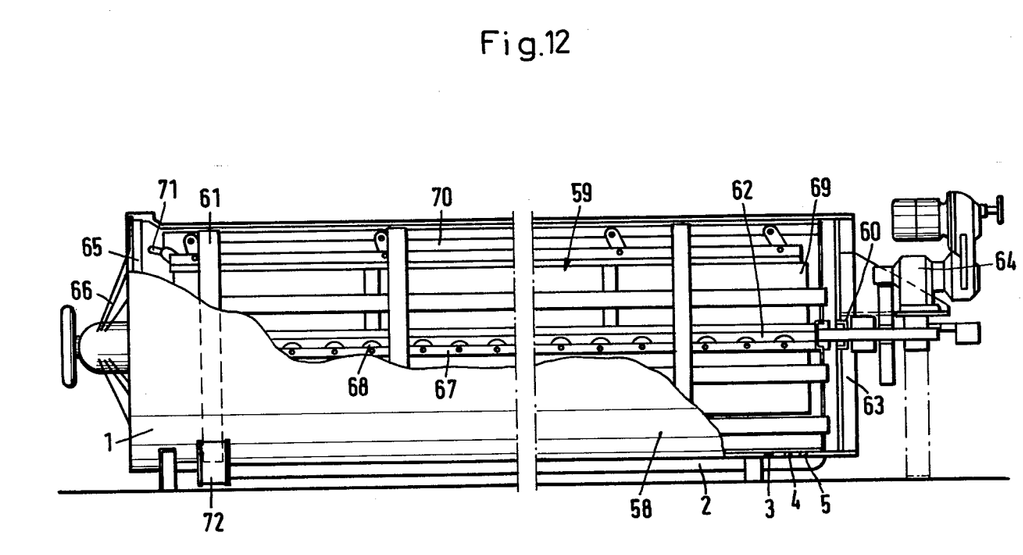
FIG. 12 is a diagrammatic side elevation showing a vessel viewed from the left in FIG. 1, partly in section.

The shell 58 of the vessel 1 shown in FIG. 1 is shown partly broken away in FIG. 12 and is provided at its lowermost generatrix with the manifold 2. The vessel contains a rotary cage 59, which is provided with a shaft 62, which extends through an end wall 63 and is sealed thereto. Outside the end wall 63, a drive unit 64 is provided, which serves to rotate the shaft 62 and the rotary cage 59. The rotary cage is supported adjacent to the end wall 63 by a shaft bearing 60. At the other end of the vessel and between its ends the rotary cage is provided with bearing rings, one of which is designated 61 and provided near the other end of the vessel. The bearing ring 61 of the rotary cage 59 revolves in rolling contact with rollers mounted in pockets 72 of the vessel 1.

At its end opposite to the end wall 63, the vessel 1 is provided with a door 65, which is adapted to be locked by a door wheel 66. The rotary cage is provided in its interior with diametrically opposite track rails 67, which carry rollers 68, which are shown in FIG. 12 in a medium height and on which so-called containers or crates can be moved into the rotary cage. These containers or crates 69 are fixed in position by a clamping mechanism 70, which has a handle indicated at 71.

Such clamping mechanism are known. FIG. 12 serves merely to show the relation of the drive unit 61 to the rotary cage 59. Such an arrangement of a rotary cage is known. The essence of the invention relates to the inlet means. A vessel provided with an internal rotary cage is shown, e.g., in U.S. Pat. No. 2,065,752, but that known vessel is provided with different inlet means. Such rotary cage is also disclosed in German Patent No. 1,165,980 and is described there as a rotary drum.

The generatrices which have been referred to are axial generatrices in accordance with the meaning of this term in connection with cylindrical members. The vessels shown in FIGS. 1 to 8 are also designed with the details shown in FIG. 12. FIGS. 1 to 8 illustrate the principle; the vessel will be provided with a central shaft 62 whenever a rotary cage is used.

In the embodiment shown in FIG. 1 the manifold 2 is connected by first conduit means 6 to a circulating pump 7, the latter is connected by second conduit means to the heater, and the latter is connected by third conduit means 9 to the manifold 10. A conduit system 75 which comprises a valve 76 opens, e.g., into the first conduit means. The conduit means 75 are connected to a source 77 of the liquid under pressure, preferably water, which is to be heated. Assemblies 7 and 8 are provided with the required electrical terminals, means for driving the pump, and the heating elements for the heater.

Figure 2:
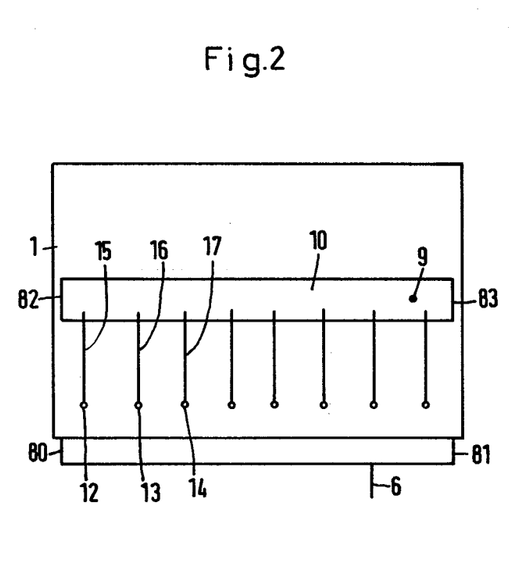
FIG. 2 is a side elevation showing the vessel of FIG. 1.

In accordance with FIG. 5, the manifold 11 is provided on its inside surface with guide means for holding the gate member 28 against the outside of the shell 58 of the vessel. The manifolds 2, 11 and the like are closed at their ends. Such end walls for the manifold 2 in FIG. 2 are designated 80, 81, and those for the manifold 10 are designated 82, 83. The manifold 11 shown in FIGS. 4 and 6 is provided with end walls 84, 85. The manifolds 38, 39 shown in FIG. 8 are also provided with closed end walls. The connections to the manifold 11 shown in FIGS. 5 and 6 are apparent from FIG. 4.

What is claimed is:

1. An autoclave, for use in sterilizing articles and using a heated liquid as the sterilizing medium and which comprises
    a vessel having a cylindrical shell, which has a horizontal central axis,
    a row of outlet openings extending through said shell and communicating with the interior of said vessel, said outlet openings being spaced apart along the lowermost generatrix of said shell,
    a row of inlet openings for supplying the heated liquid extending through said shell communicating with the interior of said vessel and spaced apart along a second generatrix of said shell, which second generatrix is angularly spaced about said shell from said lowermost generatrix by a central angle about the central axis of said shell in the range of 20° to 50°, and
    means located exteriorly of said shell for receiving liquid from said outlet openings, for heating the liquid and for returning the heated liquid to said inlet openings for circulation within said shell.

2. An autoclave as set forth in claim 1, in which
    a gate member is located on the exterior of said shell and extends in the direction of the central axis of said shell and is disposed adjacent to said inlet openings and is slidable along said second generatrix and is formed with longitudinally spaced apart apertures which register with said inlet openings and are more or less elliptical, having a major axis extending along said gate member, and
    those of said apertures in said gate member which are nearer to the ends of said vessel are more elliptical and have a longer longitudinal dimension than those of said apertures in said gate member which are more remote from the ends of said vessel,
    whereby those of said inlet openings that are more remote from the ends of said vessel have smaller ranges of exposed areas than those of said inlet openings that are nearer to the ends of said vessel.

3. An autoclave as set forth in claim 1, in which
    a second row of inlet openings extend through said shell and communicate with the interior of said vessel and are spaced apart along a third generatrix of said shell, which third generatrix is angularly spaced about said shell from said lowermost generatrix substantially by the same central angle as said second generatrix.

4. An autoclave as set forth in claim 1, in which the longitudinal axes of said inlet openings extending through said shell are tangential to said shell in a plane extending transversely of the central axis of said shell.

5. An autoclave as set forth in claim 4, in which the axes of said inlet openings extending through said shell are directed inwardly and downwardly toward said outlet openings.

6. An autoclave as set forth in claim 4, in which
    a rotatable shaft extends in said vessel on said horizontal central axis and to the outside of said vessel,
    a cage for carrying articles to be treated in said autoclave is mounted in said vessel for rotation by said shaft which extends on said central axis and to the outside of said vessel, drive means are coupled to said shaft outside said vessel and operable to rotate said shaft in a predetermined direction, and said inlet openings are arranged to feed heated liquid into said vessel in a direction which is opposite to the direction of movement of said cage past said inlet openings when said shaft is rotated in said predetermined direction.

7. An autoclave as set forth in claim 1, in which
an inlet manifold extends along the uppermost generatrix of said shell, said inlet openings located along the second generatrix being connected to said inlet manifold, and a second row of inlet openings which communicate with said inlet manifold and with the interior of said vessel are spaced apart along said uppermost generatrix.

8. An autoclave as set forth in claim 7, in which
a gate member is longitudinally slidably mounted in the axial direction of said shell in said inlet manifold on the exterior of said shell and formed with a plurality of longitudinal spaced apart apertures each in register with a respective one of said inlet openings of said second row and said gate member is longitudinally adjustable to vary the exposed areas of said inlet openings of said second row.

9. An autoclave as set forth in claim 4, in which
a rotatable shaft extends through said vessel on said horizontal central axis and to the outside of said vessel, a cage for carrying articles to be treated in said autoclave is mounted in said vessel for rotation by said shaft, drive means are coupled to said shaft outside said vessel and operable to rotate said shaft in a predetermined direction, and means are operatively connected to said inlet openings for controlling the direction of the axes of said inlet openings extending through said shell in dependence on the direction of rotation and speed of rotation of said cage about the central axis of said shell.

10. An autoclave as set forth in claim 9, in which
said control means include adjustable jet means located within said jet means, and a linkage is connected to said inlet openings and operable to adjust them in unison.

11. An autoclave as set forth in claim 4, which comprises an inlet manifold located exteriorly of said shell, a plurality of inlet pipelines located exteriorly of said shell, each of which is connected to said inlet manifold and is coaxially connected to one of said inlet openings.

12. An autoclave as set forth in claim 11, in which said inlet openings are defined by nozzles having flow paths which are constricted relative to said inlet pipelines.

13. An autoclave system, which comprises
a vessel having a cylindrical shell, which has a horizontal central axis, a row of outlet openings extending through said shell and spaced apart along the lowermost generatrix of said shell and communicating with the interior of said vessel, an outlet manifold extending outside said vessel and communicating with
said row of outlet openings, a row of inlet openings extending through said shell and communicating with the interior of said vessel and spaced apart along a second generatrix of said shell, said second generatrix being angularly spaced around said shell from said lowermost generatrix by a central angle about the central axis of said shell in the range of 20° to 50°, an inlet manifold extending outside said vessel, and spaced angularly from the second generatrix, a plurality of pipelines, each of which connects said inlet manifold to one of said inlet openings, and a recirculating system, which connects said outlet manifold to said inlet manifold and incorporates a heater for heating liquid and a circulating pump for recycling liquid from said outlet manifold through said heater to said inlet manifold for supplying heated liquid to said shell.

14. An autoclave system as set forth in claim 13, in which said recirculating system comprises
first conduit means connecting said outlet manifold to said circulating pump, second conduit means connecting said circulating pump to said heater, and third conduit means connecting said heater to said inlet manifold.

15. An autoclave system as set forth in claim 14, in which
at least one additional inlet manifold is provided, which extends along said shell outside said vessel, additional inlet openings are provided, which communicate with the interior of said vessel and with said at least one additional inlet manifold and are spaced apart along at least one additional generatrix of said shell to form at least one additional row of inlet openings, and said third conduit means comprise a plurality of conduits, each of which connects said heater to one of said inlet manifolds.

16. An autoclave system as set forth in claim 14 in which
said inlet manifold is disposed adjacent to the lower half of said shell and above said second generatrix, said inlet pipelines extend downwardly from said inlet manifold to said inlet openings and said inlet openings are defined by nozzles having longitudinal axes substantially tangential to said shell in a plane extending transversely of said shell, and each of said inlet pipelines is substantially coaxially connected to one of said inlet openings.

17. An autoclave system as set forth in claim 16, in which
a shaft extends through said vessel on said horizontal central axis and to the outside of said vessel, a cage for carrying articles to be treated in said autoclave system is mounted in said vessel for rotation by said shaft, drive means are coupled to said shaft outside said vessel and operable to rotate said shaft, and means are provided for controlling the direction of the axes of said inlet openings in dependence on the direction of rotation and speed of rotation of said cage.

* * * * *